(12) United States Patent
Imai et al.

(10) Patent No.: US 12,313,509 B2
(45) Date of Patent: May 27, 2025

(54) SAMPLE SOLUTION PREPARATION METHOD FOR MEASUREMENT BY IMMUNITY ANALYSIS METHOD USING FLUORESCENCE, MEASUREMENT CELL, MEASUREMENT KIT, AND SAMPLE SOLUTION PREPARATION DEVICE

(71) Applicant: TIANMA JAPAN, LTD., Kanagawa (JP)

(72) Inventors: Ayuko Imai, Kawasaki (JP); Ken Sumiyoshi, Kawasaki (JP)

(73) Assignee: TIANMA JAPAN, LTD., Kanagawa (JP)

( * ) Notice: Subject to any disclaimer, the term of this patent is extended or adjusted under 35 U.S.C. 154(b) by 4 days.

(21) Appl. No.: 17/221,231

(22) Filed: Apr. 2, 2021

(65) Prior Publication Data

US 2021/0310912 A1   Oct. 7, 2021

(30) Foreign Application Priority Data

Apr. 6, 2020   (JP) .................................. 2020-068486

(51) Int. Cl.
*G01N 1/40* (2006.01)
*G01N 1/28* (2006.01)
(Continued)

(52) U.S. Cl.
CPC .......... *G01N 1/4005* (2013.01); *G01N 1/286* (2013.01); *G01N 21/6428* (2013.01);
(Continued)

(58) Field of Classification Search
CPC ................. G01N 1/286; G01N 1/4005; G01N 2021/6439; G01N 2021/8466;
(Continued)

(56) References Cited

U.S. PATENT DOCUMENTS 4,344,438 A * 8/1982 Schultz ................ A61B 5/1459
600/341
2002/0026108 A1* 2/2002 Colvin, Jr. ......... G01N 21/7703
128/903
(Continued)

FOREIGN PATENT DOCUMENTS

JP   H03-103765 A   4/1991
JP   H11-503521 A   3/1999

OTHER PUBLICATIONS

Müller, Eckart, Rosemarie Berger, Eckhart Blass, Domien Sluyts, and Andreas Pfennig. "Liquid-liquid extraction." Ullmann's Encyclopedia of Industrial Chemistry (2000). (Year: 2000).*
(Continued)

*Primary Examiner* — Elizabeth A Robinson
*Assistant Examiner* — Brittany I Fisher
(74) *Attorney, Agent, or Firm* — Sughrue Mion, PLLC

(57) ABSTRACT

A sample solution preparation method, a measurement cell, a measurement kit, and a sample solution preparation device for measuring a target compound contained in food by an immunity analysis method using fluorescence. The present disclosure features including a dialysis step for bringing a target compound-containing solution that includes the target compound into contact with a dialysis fluid through a dialysis membrane to transfer the target compound to the dialysis fluid, in which the molecular weight cut-off of the dialysis membrane is within a range of $2\times10^2$ to $2\times10^5$, and the volume of the dialysis fluid is relatively smaller than the volume of the target compound-containing solution.

10 Claims, 14 Drawing Sheets

(51) Int. Cl.
  *G01N 21/64* (2006.01)
  *G01N 33/02* (2006.01)
  *G01N 33/12* (2006.01)
  *G01N 33/53* (2006.01)
  *G01N 33/58* (2006.01)

(52) U.S. Cl.
  CPC .............. *G01N 33/02* (2013.01); *G01N 33/12* (2013.01); *G01N 2021/6439* (2013.01)

(58) Field of Classification Search
  CPC .......... G01N 21/6428; G01N 21/6445; G01N 33/02; G01N 33/12
  See application file for complete search history.

(56) References Cited

U.S. PATENT DOCUMENTS

| | | | | |
|---|---|---|---|---|
| 2009/0220940 A1* | 9/2009 | Lev | .................. | B01D 65/102 435/235.1 |
| 2016/0340717 A1* | 11/2016 | McNamara | ............ | C07H 21/02 |

OTHER PUBLICATIONS

Nakanishi, Koichiro, and Michio Kurata. "Density measurement in dilute aqueous solution of polyvinyl alcohol." Bulletin of the Chemical Society of Japan 33, No. 2 (1960): 152-157. (Year: 1960).*
Chiou, Jau-Rung, Bo-Hung Lai, Kai-Chih Hsu, and Dong-Hwang Chen. "One-pot green synthesis of silver/iron oxide composite nanoparticles for 4-nitrophenol reduction." Journal of hazardous materials 248 (2013): 394-400. (Year: 2013).*
Benes, P., and E. Steinnes. "In situ dialysis for the determination of the state of trace elements in natural waters." Water Research 8, No. 11 (1974): 947-953. (Year: 1974).*
www.epa.gov/mercury/guidelines-eating-fish-contain-mercury Retrived May 11, 2023 (Year: 2019).*
Akhond, et al., "Studying the Adsorption Process of Riboflavin on Silver-Deposited Fe3O4 Nanoparticles", Analytical and Bioanalytical Chemistry Research, Dec. 2016, vol. 3, No. 2, pp. 225-237 (13 pages).
Huo et al., "Modern Food Nutrition and Safety", Beijing: China Light Industry Press, Aug. 1, 2005 pp. 137-138 (3 pages).
Communication dated Feb. 27, 2025 in Chinese Application No. 202110360748.2.

* cited by examiner

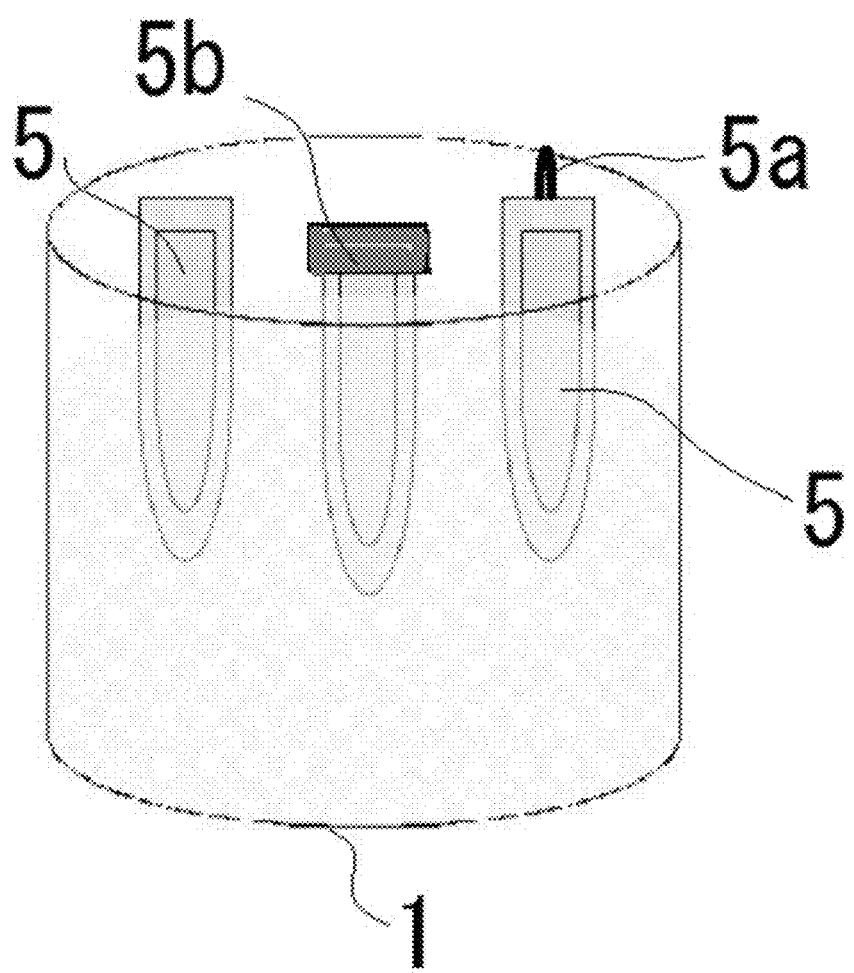

SAMPLE SOLUTION PREPARATION METHOD FOR MEASUREMENT BY IMMUNITY ANALYSIS METHOD USING FLUORESCENCE, MEASUREMENT CELL, MEASUREMENT KIT, AND SAMPLE SOLUTION PREPARATION DEVICE

CROSS-REFERENCE TO RELATED APPLICATION

This application claims the benefit of Japanese Patent Application No. 2020-068486, filed on Apr. 6, 2020, the entire disclosure of which is incorporated by reference herein.

FIELD

The present disclosure relates to a sample solution preparation method for measuring the concentration of a target compound included in food by an immunity analysis method using fluorescence, a measurement cell, a measurement kit, and a sample solution preparation device.

BACKGROUND

Fluorescence polarization immunoassay (FPIA) is known as an immunity analysis method using fluorescence that detects target substances utilizing antigen-antibody reactions. Unexamined Japanese Patent Application Publication No. H03-103765 describes the principle of a fluorescence polarization immunoassay method where a sample is irradiated with excitation light and, among polarized components that are emitted from the sample, a polarized component that is parallel to the polarized direction of the incident light and a polarized component that is perpendicular to the polarized direction of the incident light are measured, and the degree of polarization is calculated using the two polarized components. Since the degree of fluorescence polarization is proportional to the effective volume of the target substance, the value becomes large corresponding to the molecular weight of the substance. For this reason, a target substance preferably has a low molecular weight. Unexamined Japanese Patent Application Publication (Translation of PCT Application) No. H11-503521 discloses a method of measuring vancomycin by FPIA, which makes it possible to avoid measurement errors caused by mixing of vancomycin analogues, by setting a vancomycin with a molecular weight lower than the molecular weight of an antigen protein as a target substance and preparing a monoclonal antibody that specifically binds to the vancomycin.

Substances that are included in food and cause a problem depending on the content include mold poisons, shellfish poisons, chemicals used for breeding animals, chemicals used for growing crops, and the like. It is important to prevent food poisoning and evaluate agrochemical residues and the like in food to ensure food safety. Deoxynivalenol (DON), a mold poison that infects wheats and other grains, has been conventionally measured by liquid chromatography-tandem mass spectrometry (LC/MS), yet, can be similarly measured as vancomycin using FPIA if the corresponding antibody can be prepared. Although blood vancomycin concentration is measured, after blood sampling, in a laboratory specifically handling medical specimens, food contamination is preferably measured on site. Since food includes high in fat, sugar, protein and other impurities, it is necessary to extract fractions containing a mold poison from various foods and prepare samples that are concentrated enough to be measured by FPIA. In addition, target compounds that are considered problematic under food safety laws are not only limited to mold poisons but also include agrochemical residues. Furthermore, in the livestock and fisheries industries, there are products that claim to be antibiotic-free and antibacterial agent-free, with the motto of "healthy breeding." It is also important to measure concentrations of antibiotics and antibacterial agents included in meat and fish grown in such a way as target compounds and evaluate safety of the meat and fish. Thus, there is a need for a method for preparing samples that allows on-site detection of target compounds, such as mold poisons and agrochemical residues contained in food, by an immunity analysis method using fluorescence.

In addition to FPIA, immunity analysis methods using fluorescence include fluorescence enzyme immunoassay (FEIA), in which an antigen-antibody reaction is performed using an antigen or antibody that is enzyme-labeled as a labeled substance and the fluorescence intensity is measured by adding a fluorogenic substance, and fluorescent antibody method (FA), in which an antibody that specifically recognizes an antigen is used to examine the distribution of the antigen. Since immunity analysis methods using fluorescence can detect trace elements, the need for on-site sample preparation is not limited to FPIA, but also applies to FEIA, FA, and other immunity analysis methods using fluorescence.

SUMMARY

The sample solution preparation method is a sample solution preparation method for measuring the concentration of a target compound contained in food by an immunity analysis method using fluorescence, the sample solution preparation method includes:
  a dialysis step for bringing a target compound-containing solution that includes the target compound into contact with a dialysis fluid through a dialysis membrane to transfer the target compound to the dialysis fluid, wherein
  the molecular weight cut-off of the dialysis membrane is within a range of $2 \times 10^2$ to $2 \times 10^5$, and
  the volume of the dialysis fluid is relatively smaller than the volume of the target compound-containing solution.

The measurement cell is a measurement cell for measuring a concentration of a target compound contained in food by an immunity analysis method using fluorescence and comprises:
  a measurement area comprising a member that transmits a wavelength within a range of 300 to 800 nm; and
  a dialysis membrane with a molecular weight cut-off within a range of $2 \times 10^2$ to $2 \times 10^5$.

The measurement kit is measurement kit for measuring a concentration of a target compound selected from a group consisting of a mold poison, a shellfish poison, a chemical used for breeding animals, and a chemical used for growing crops contained in food by an immunity analysis method using fluorescence, the measurement kit comprising:
  the above mentioned measurement cell;
  a dialysis fluid to be charged in the measurement cell;
  an antibody that specifically binds to the target compound; and
  a fluorescently labeled target compound derivative.

The sample solution preparation device is a sample solution preparation device in an immunity analysis method using fluorescence and comprises:

a container that receives a target compound-containing solution; and one or more dialysis cartridges that are placed in the container, wherein the ratio of the total capacity of the dialysis cartridges to the capacity of the container (the total capacity of the dialysis cartridges/the capacity of the container) is within a range of $1/1\times10^4$ to $1/10$.

It is to be understood that both the foregoing general description and the following detailed description are exemplary and explanatory and are not restrictive of this disclosure.

BRIEF DESCRIPTION OF THE DRAWINGS

A more complete understanding of this application can be obtained when the following detailed description is considered in conjunction with the following drawings, in which:

FIG. 9A is a diagram describing a mode in which a sample solution preparation device includes a plurality of dialysis cartridges arranged in a container and the dialysis cartridges are equipped with a stopper or a lid;

FIG. 11 is a diagram illustrating the results of Example 1;

FIG. 12 is a diagram illustrating the results of Example 2; and

DETAILED DESCRIPTION

Figure 1:
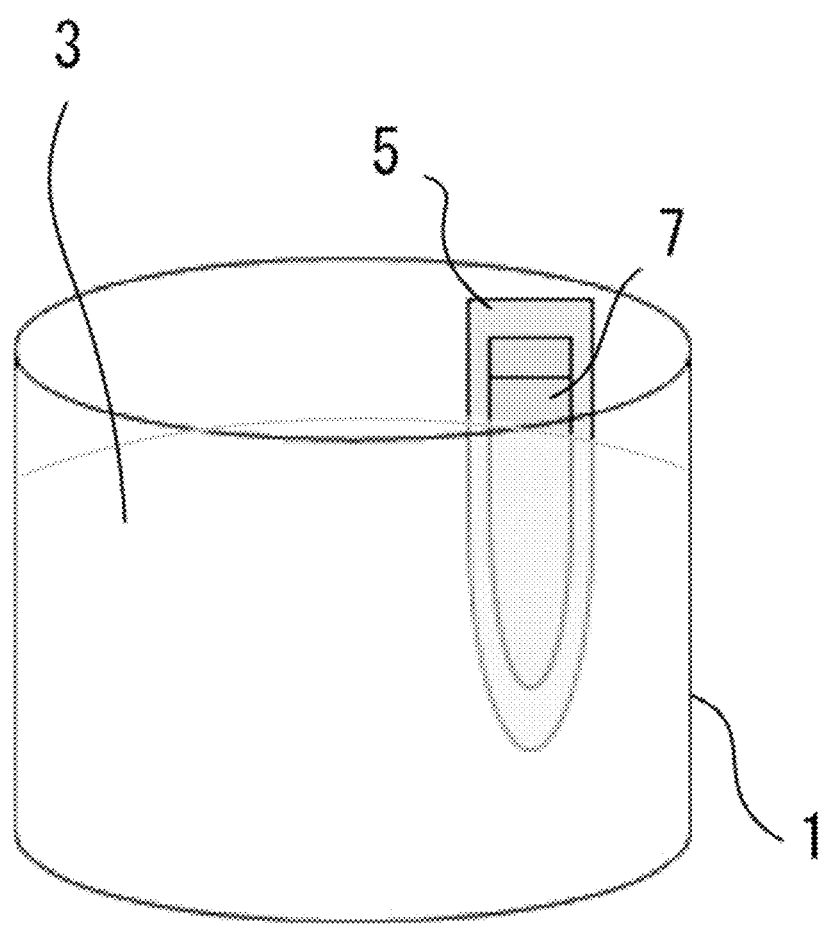
FIG. 1 is a diagram illustrating a mode in which a dialysis cartridge charged with a dialysis fluid is immersed in an extraction container receiving a target compound-containing solution.

A first embodiment of the present disclosure is a sample solution preparation method for measuring the concentration of a target compound contained in food by an immunity analysis method using fluorescence, the sample solution preparation method includes a dialysis step for bringing a target compound-containing solution that includes the target compound into contact with a dialysis fluid through a dialysis membrane to transfer the target compound to the dialysis fluid, wherein the molecular weight cut-off of the dialysis membrane is within a range of $2\times10^2$ to $2\times10^5$, and the volume of the dialysis fluid is relatively smaller than the volume of the target compound-containing solution.

Immunity analysis methods using fluorescence include FEIA, FA and FPIA, all of which are in the scope of the present disclosure. The following will describe the case of FPIA for convenience of explanation.

FPIA is based on the principle of competitive binding immunoassay. Two kinds of reagents are used: a fluorescently labeled compound obtained by labelling the same molecule as a target molecule with a fluorescent material; and an antibody that specifically binds to the target molecule. These fluorescently labeled compound and antibody, as well as, a measurement target solution are added in a measurement cell, the cell is irradiated with excitation light, a polarized component (Ih) that is emitted from the sample and parallel to the polarized direction of the incident light and a polarized component (Iv) that is emitted from the sample and perpendicular to the polarized direction of the incident light are measured, and the degree of fluorescence polarization P=(Ih−Iv)/(Ih+Iv) is calculated. Since the degree of fluorescence polarization P varies depending on the concentration of the target molecule, the concentration of the target molecule can be detected, for example, using a previously prepared calibration curve. As FPIA uses specific reactions with antibodies, FPIA can reduce measurement errors caused by analogues such as metabolites, compared to the conventional LC/MS (/MS) method or the like.

The target compound in the present disclosure may be any compound without particular limitation that is contained in food and measurable by an immunity analysis method using fluorescence. However, since the immunity analysis method using fluorescence allows detection of compounds at low concentrations, the method is preferable for measurement of compounds that affect a living body at low concentrations, such as mold poisons, shellfish poisons, chemicals used for breeding animals, chemicals used for growing crops and the like, contained in food.

Mold poison include micotoxins such as aflatoxin, ochratoxin, deoxynivalenol, zearalenone, fumonisin, patulin, citrinin, T-2 toxin, and HT2 toxin, and alkaloids such as ergot alkaloid and tropane alkaloid.

Shellfish poisons include okadaic acid, domoic acid, and saxitoxin.

Further, chemicals used for breeding animals include: tetracycline antibiotics such as tetracyclines, oxytetracyclines, chlortetracyclines, and limecyclines; nitrofurans such as nitrofurazone, nitrofurantoin, furazolidone, and furaltadone; antibiotics such as chloramphenicol; antibacterial agents such as malachite green, gentiana violet, and enrofloxacin; and growth promoters such as lactopamine, clenbuterol, diethylstilbestrol, and salbutamole.

Furthermore, chemicals used for growing crops include agrochemicals such as imidacloprid, fenitrothion, chlorfenapyr, and chlorotalonil.

Foods include: grains such as rice, wheat, barley, and beans; vegetables such as spinach, tomatoes, and carrots; frozen foods such as frozen spinach, frozen green soybeans, and frozen carrots; beverages such as milk, water, and liquor; seasonings such as soy sauce and other sauces; meat such as chicken and pork; fish such as bristle, snapper, tuna, and eel; shellfish such as oysters and scallops; and processed foods containing these.

In the sample solution preparation method of the present disclosure, a solution containing a target compound is referred to as a target compound-containing solution, and this target compound-containing solution is brought into contact with a dialysis membrane to transfer the target compound to a dialysis fluid. The target compound-containing solution may be a food itself or may be a solution obtained by mixing a food or a ground food with a solvent. Liquid food, such as beverages and liquid seasonings, can be brought into contact with the dialysis membrane as they are. Whereas, if the food is solid or semisolid, it is preferable to extract the target compound in a solvent in advance. For example, a solution obtained by adding a solvent to a food and mixing the solvent and food, a solution obtained by grinding a food in advance and mixing the ground food with a solvent, and a solution obtained by adding a solvent to a food and homogenizing the solvent and food, can be used as a target compound-containing solution. The grinding degree for grinding a food may be, for example, a grinding degree that is applied when preparing samples by the LC/MS (/MS) method. The extraction time from a food to a solvent varies depending on a food, a target compound, and a solvent used, and, thus, the optimal condition can be selected by measuring extraction times and extraction rates in advance. If a target compound-containing solution contains insoluble substances, such as cellulose, chitin, and chitosan, such insoluble substances may be removed in advance by centrifugation, static separation, filtration, or the like.

Examples of the solvent to be added to food include water; alcohols such as methanol, ethanol, and butanol; ketones such as acetone, diethyl ketone, and methyl amyl ketone; alkanes such as hexane and heptane; ethers such as diethyl ether; methyl sulfoxide; acetonitrile; chloroform; and a mixed solvent of these. As the solvent for extracting a target compound, solvents that are used for measurement by the LC/MS (/MS) method may be selected and used as necessary. For example, to prepare a sample for measuring DON contained in wheat, a mixture solution of acetonitrile:water:methanol=5:95:5 can be used, and, to extract chloramphenicol as a chemical used for breeding animals, methanol can be used. It should be noted that a solvent that is different from solvents for preparing samples used by the conventional LC/MS (/MS) method may also be used.

The dialysis membrane used in the present disclosure can be one with a molecular weight cut-off of $2 \times 10^2$ to $2 \times 10^5$. The molecular weight cut-off is preferably within a range of $2 \times 10^2$ to $1.4 \times 10^5$, more preferably $1.5 \times 10^4$ to $1.4 \times 10^5$. The target compound-containing solution may contain salts such as Tris and PBS, reducing agents such as DTT and β-mercaptoethanol, and preservatives such as sodium azide and timerosar, which may act as inhibitors that cause measurement errors during measurement by FPIA. Thus, the lower limit of the molecular weight cut-off is set to $2 \times 10^2$ in order to eliminate these compounds. On the other hand, since a substance having a molecular weight of more than $2 \times 10^5$ has a light scattering property, such a substance is likely to cause a measurement error in FPIA. Thus, the upper limit of permeation of the molecular weight cut-off is set to $2 \times 10^5$. Examples of such a dialysis membrane include a dialysis tube made of cellulose ester and a dialysis tube made of synthetic polymer, such as polymethylmethacrylate and polysulfone.

Other than the molecular weight cut-off, the dialysis membrane that is used in the present disclosure can preferably be a membrane with organic solvent resistance.

The volume of the dialysis fluid is characteristically smaller than the volume of the target compound-containing solution. For example, when the solubility of the target compound is equal in both the target compound-containing solution and the dialysis fluid, and the target compound migrates uniformly to both sides, the target compound content contained in the dialysis fluid can be approximate to the target compound content contained in the target compound-containing solution by making the ratio of the volume of the dialysis fluid to the volume of target compound-containing solution (the volume of the dialysis fluid/the volume of the target compound-containing solution) smaller. For example, if the ratio between the dialysis fluid and the target compound-containing solution is 1/100, the concentration of the target compound contained in the dialysis fluid at dialysis equilibrium becomes 0.99 times the concentration of the target compound contained in the target compound-containing solution, where the sample for measurement can be prepared with almost no dilution. The ratio of the volume of the dialysis fluid to the volume of the target compound-containing solution (the volume of the dialysis fluid/the volume of the target compound-containing solution) is within a range of $1/1 \times 10^4$ to $1/10$, preferably, $1/1 \times 10^4$ to $1/1 \times 10^2$, more preferably $1/1 \times 10^3$ to $1/1 \times 10^2$.

The dialysis time varies depending on a dialysis membrane used, a solvent used, and a target compound, and, thus, the optimal condition can be selected by measuring dialysis times and dialysis rates in advance.

As such a dialysis membrane, for example, a dialysis cartridge equipped with a dialysis membrane on its outer circumference can be used. An example of this mode is illustrated in FIG. 1. A dialysis cartridge 5 charged with a dialysis fluid 7 is immersed in an extraction container 1 receiving a target compound-containing solution 3. The target compound contained in the target compound-containing solution 3 transfers to the side of the dialysis fluid 7 through the dialysis membrane while salts and the like cannot, thereby obtaining the dialysis fluid 7 from which salts and light diffusing substances and the like have been removed. Further, with the dialysis cartridge 5, the ratio of the volume of the dialysis fluid to the volume of the target compound-containing solution can be easily adjusted. FIG. 1 illustrates a mode in which the volume of the target compound-containing solution 3 is significantly larger than the volume of the dialysis fluid 7. This enables preparation of a sample solution in which the concentration of the target compound contained in the target compound-containing solution is maintained.

Figure 2:
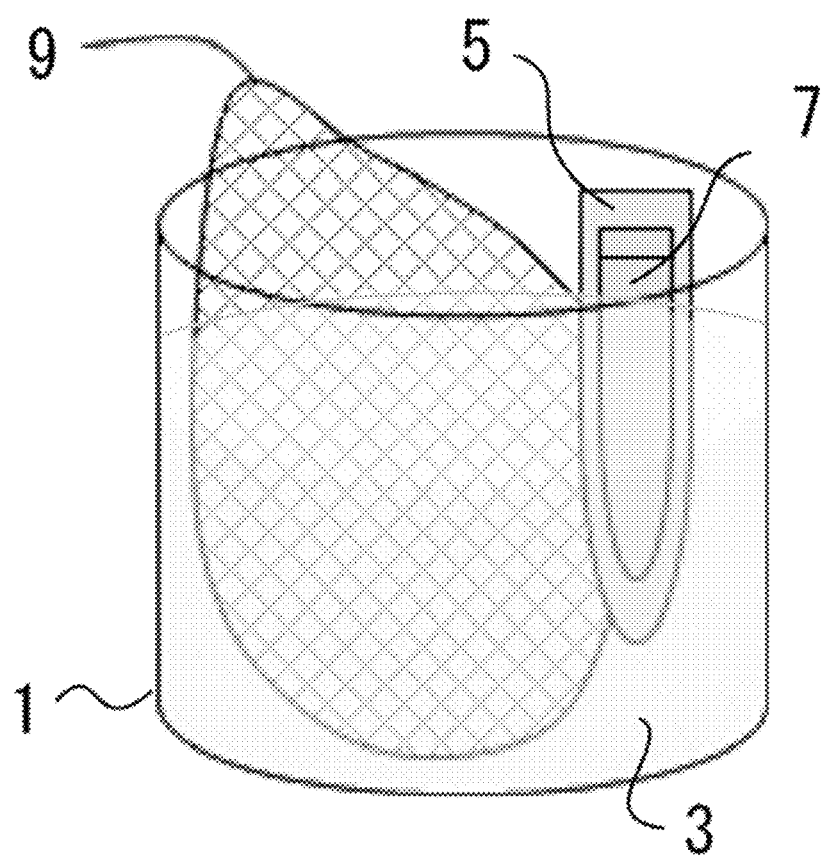
FIG. 2 is a diagram illustrating a mode in which a ground food sample is placed in a filter bag and immersed in a solvent to prepare a target compound-containing solution that is simultaneously dialyzed by a dialysis cartridge.

FIG. 2 illustrates a mode in which a bag filter 9 receives a ground food sample, which is then immersed in a solvent to make a target compound-containing solution 3. Extraction of a target compound from a food, as well as, dialysis by a dialysis cartridge 5 can be simultaneously performed, thereby reducing sample solution preparation time.

Figure 3:
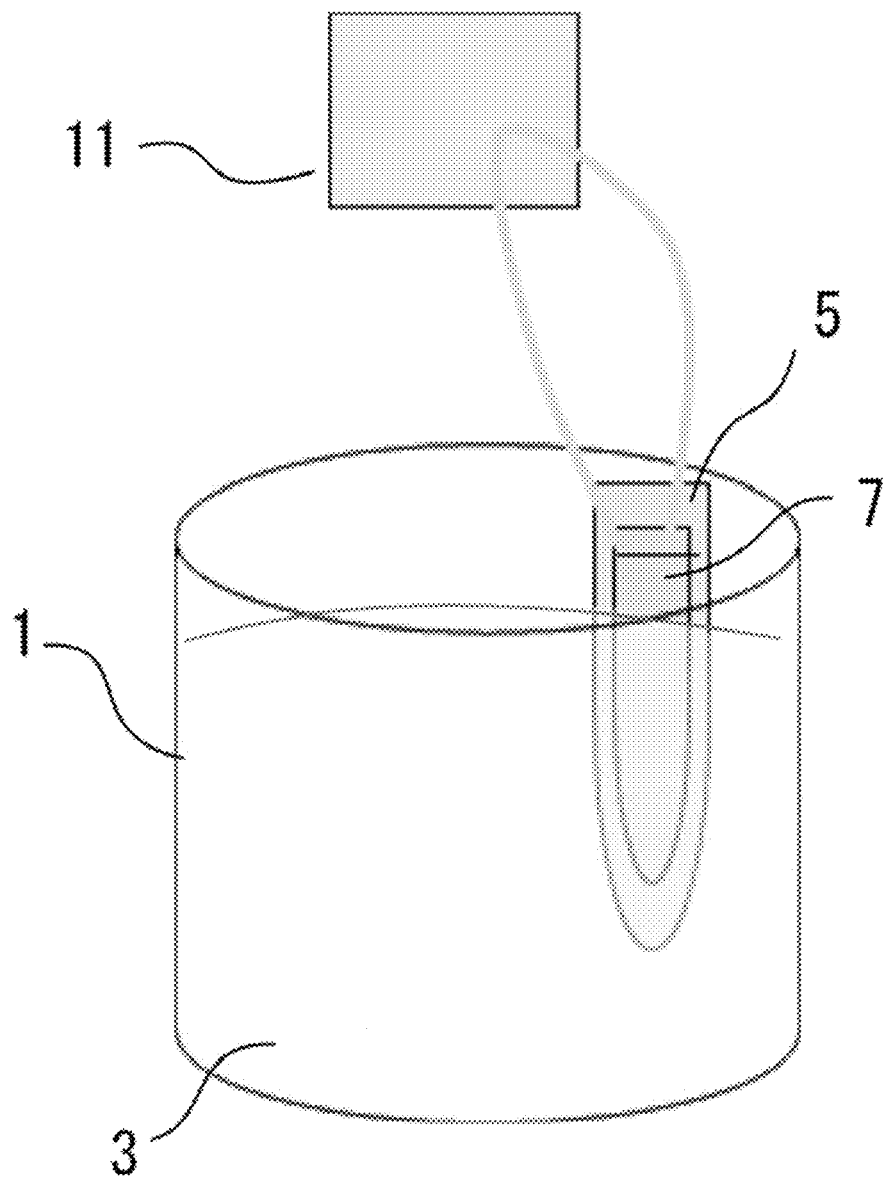
FIG. 3 is a diagram describing a mode in which a dialysis cartridge is equipped with a heater.

The dialysis step can also be performed under a condition where the temperature of a dialysis fluid is higher than the temperature of a target compound-containing solution. In general, solubility increases as the temperature of a solvent rises. Accordingly, raising the fluid temperature of a dialysis fluid higher than the fluid temperature of a target compound-containing solution, can transfer a high concentration of a target compound to the side of the dialysis fluid. FIG. 3 illustrates an example of a mode in which a dialysis fluid 7 in a dialysis cartridge 5 is heated by a heater 11. For example, the fluid temperature of the dialysis fluid 7 can be raised by inserting heating equipment in the dialysis cartridge 5. The temperature difference between the target compound-containing solution 3 and the dialysis fluid 7 varies depending on a target compound, a solvent used, the type of a dialysis membrane, and the dialysis fluid 7, and, thus, the optimal condition can be selected by measuring dialysis times and dialysis rates at various temperature differences in advance.

In the present disclosure, as a solvent used when mixing food or its ground matter with the solvent, a solvent having different solubility for a target compound than a dialysis fluid may be used. For example, if the solubility of solvent A for a target compound is lower than the solubility of solvent B for the target compound, solvent A is used to prepare a target compound-containing solution and solvent B is used for a dialysis fluid. Since ethanol-containing water has higher solubility for chloramphenicol than water does, ethanol-containing water is used as a dialysis fluid when detecting chloramphenicol as a target compound from milk. Also, when dialysis is performed by setting the ratio of the volume of a dialysis fluid to the volume of a target compound-containing solution (the volume of the dialysis fluid/the volume of the target compound-containing solution) to 1/100, the concentration of the target compound contained in the dialysis fluid can be 0.99 times or more the concentration of the target compound contained in the target compound-containing solution at dialysis equilibrium.

Figure 4:
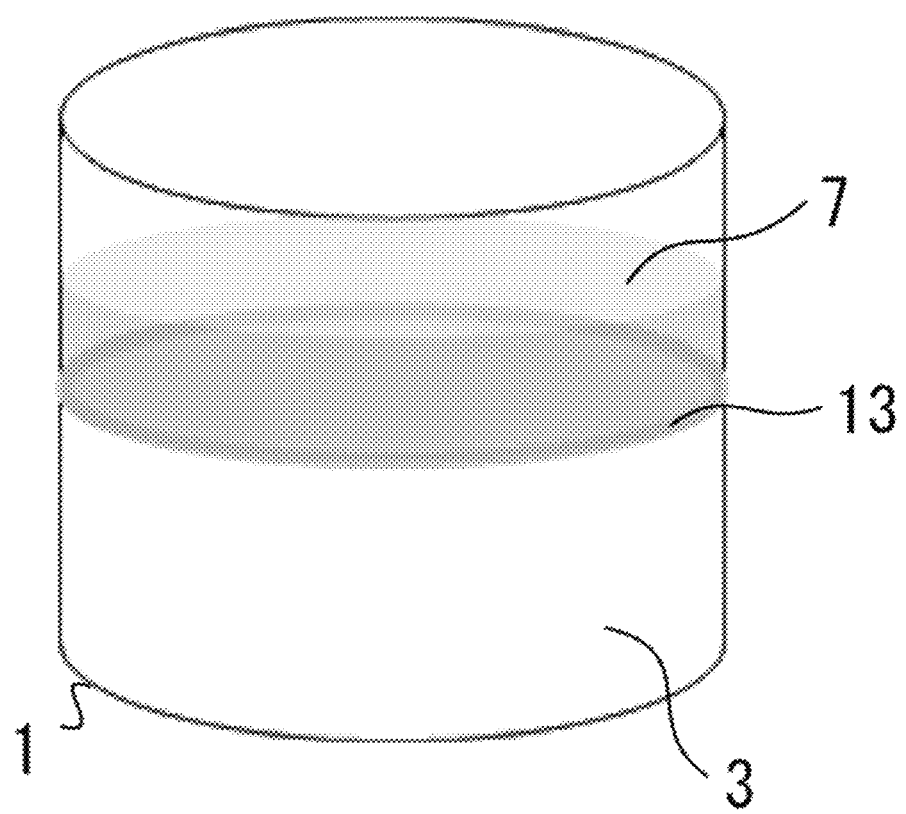
FIG. 4 is a diagram describing a mode in which a target compound-containing solution having a higher specific gravity is placed at a lower layer, a dialysis membrane is placed on top of the lower layer, and a dialysis fluid is charged onto the upper surface of the dialysis membrane.

Contact between a target compound-containing solution and a dialysis fluid through a dialysis membrane is not limited to the use of the dialysis cartridge described above. Particularly when the specific gravities of a target compound-containing solution and a dialysis fluid are different, the fluid having a heavier specific gravity may be placed at a lower layer, the dialysis membrane may be placed on top of the lower layer, and the fluid having a lighter specific gravity may be poured onto the dialysis membrane to transfer the target compound to the dialysis fluid. FIG. 4 illustrates an example of a mode in which a target compound-containing solution 3 is placed at a lower layer and a dialysis fluid 7 is charged onto the upper surface of a dialysis membrane 13. For example, when doxycycline is measured as a target compound, the target compound-containing solution 3 is prepared, for example, by mixing a ground matter of pork as a food with water, and, if chloroform is used as the dialysis fluid 7, chloroform is placed at a lower layer, the dialysis membrane 13 is allowed to stand on the upper surface of the lower layer, and the target compound-containing solution 3 is charged on top of the dialysis membrane 13. This mode is effective for such a target compound, for chloroform has higher solubility for doxycycline than water does.

Figure 5:
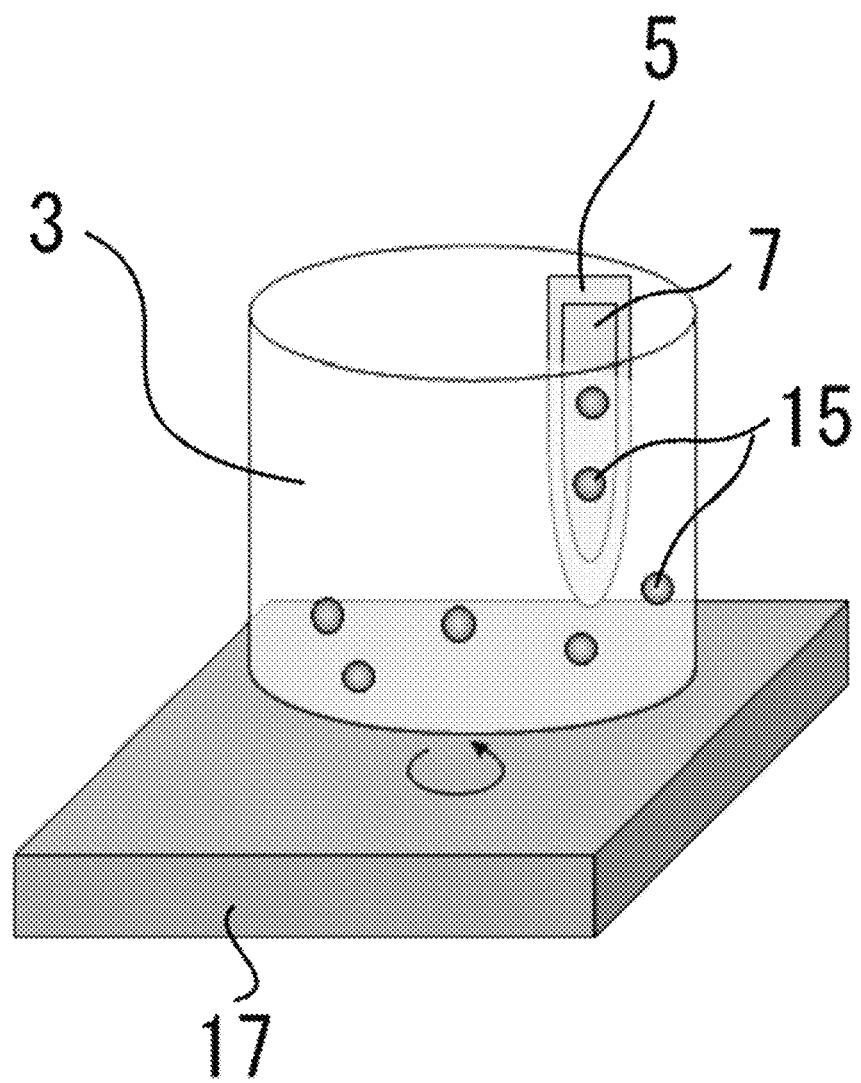
FIG. 5 is a diagram describing a mode in which a target compound-containing solution is received in a container placed on a magnetic stirrer, a dialysis cartridge is immersed in this solution, and iron oxide particles containing silver particles are added to both the solution and the dialysis fluid; when the magnetic stirrer is driven, the iron oxide particles containing silver particles rotate according to the rotation of the motor, thereby agitating both the solution and the dialysis fluid.

In the present disclosure, the dialysis step may be performed while agitating a target compound-containing solution and a dialysis fluid with a stirrer chip that includes iron oxide particles containing silver particles. It is a well-known technique to rotate a stirrer chip using magnetic force to agitate a fluid. Agitating the target compound-containing solution and dialysis fluid with iron oxide particles containing silver particles can shorten dialysis equilibrium time. Such iron oxide particles containing silver particles include silver-coated iron oxide particles and silver-iron oxide particles. The particle size is not limited, but is preferably within a range of 0.1 to 10 μm in diameter, more preferably 1 to 10 μm in diameter. In particular, it was found that when iron oxide particles containing silver particles are used as the stirrer chip, fluorescent substances, such as riboflavin, contained in the target compound-containing solution and dialysis fluid can be adsorbed. The molecular weight of riboflavin is 376, which is close to the molecular weight of the target compound. As such, even when riboflavin permeates the dialysis membrane, riboflavin contained in the solution is adsorbed by the iron oxide particles containing silver particles, whereby a sample solution with less measurement errors can be prepared. FIG. 5 illustrates a mode in which a container 1 placed on the upper surface of a magnetic stirrer 17 receives a target compound-containing solution 3, a dialysis cartridge 5 is immersed in this solution, and iron oxide particles containing silver particles 15 are added to both the solution and the dialysis fluid. When the magnetic stirrer 17 is driven, the iron oxide particles containing silver particles 15 are aggregated, and when the magnetic stirrer 17 is stopped, the iron oxide particles containing silver particles 15 are dispersed, whereby both the solution and the dialysis fluid are agitated.

Figure 6:
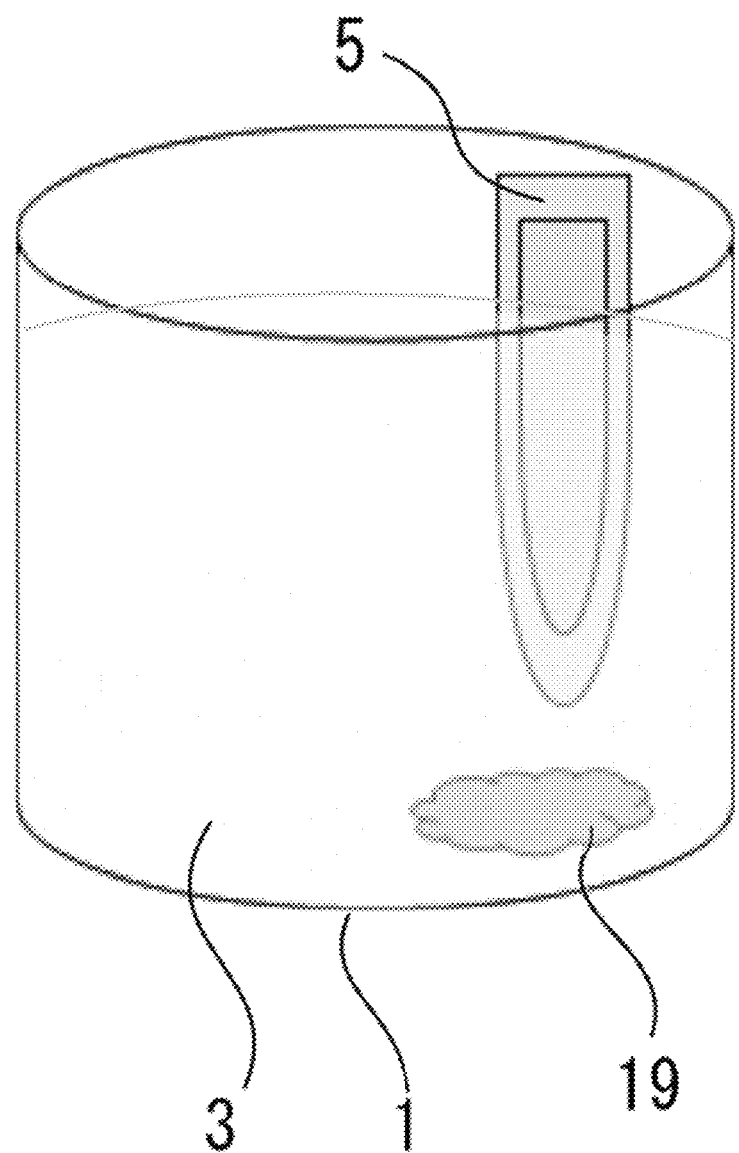
FIG. 6 is a diagram describing a mode in which a dialysis cartridge is immersed in a target compound-containing solution received in a container with an adsorbent placed on the bottom of the container.

In the present disclosure, the dialysis step may be performed by adding impurity adsorbent in a target compound-containing solution. Such impurities include neutral fats, cholesterol, phospholipids, free fatty acids having 5 to 30 carbon atoms, fluorescent substances such as vitamin B2, and light scattering materials such as protein micelles. Examples of such an adsorbent include gelatin, lime, protein, and bentonite. The optimum condition for the amount of the adsorbent used can be selected by evaluating the kinds of impurities to be removed and the contents of the impurities in advance. FIG. 6 illustrates a mode in which a dialysis cartridge 5 is immersed in a target compound-containing solution 3 received in a container 1, and an adsorbent 19 is placed on the bottom of the container 1. The adsorbent may be, for example, granular particles having a particle size of 0.1 to 5 mm or may be a mode in which the granular particles are mixed with a target compound-containing solution. With this particle size, the adsorbent does not permeate the dialysis membrane and can efficiently adsorb impurities.

A second embodiment of the present disclosure is a measurement cell for measuring the concentration of a target compound contained in food by an immunity analysis method using fluorescence, in which a measurement area made of a member that transmits a wavelength within a range of 300 to 800 nm and a dialysis membrane with a molecular weight cut-off of $2 \times 10^2$ to $2 \times 10^5$ are arranged. In the present disclosure, an example of using a dialysis cartridge as a dialysis membrane has been described. Because, if such a dialysis cartridge can be used as it is as a measurement cell, sample preparation and measurement can be performed by a series of operations. The measurement cell according to the present disclosure is characterized by including a dialysis membrane useful for sample preparation and a measurement area useful for fluorescence measurement.

Figure 7:
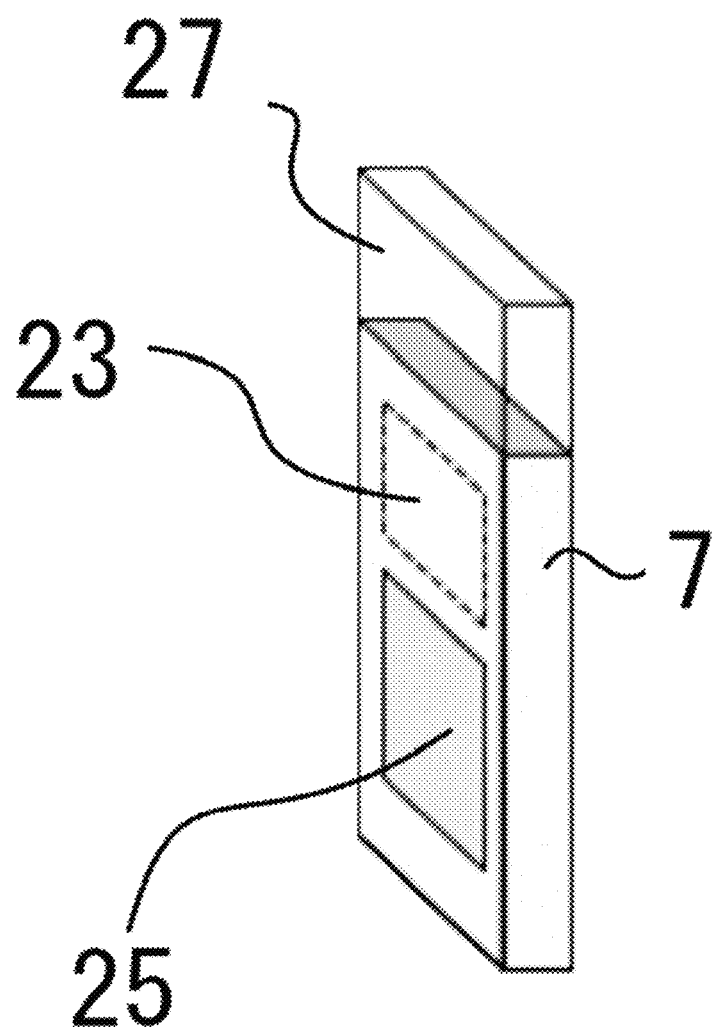
FIG. 7A is a diagram describing an example of a preferred mode of a rectangular measurement cell; a measurement area that transmits excitation light is arranged above the measurement cell and a dialysis membrane is arranged below the measurement cell.
FIG. 7B is a diagram describing a use method of the measurement cell; a dialysis fluid is charged in the measurement cell, which is then immersed in a target compound-containing solution.
Figure 7B:
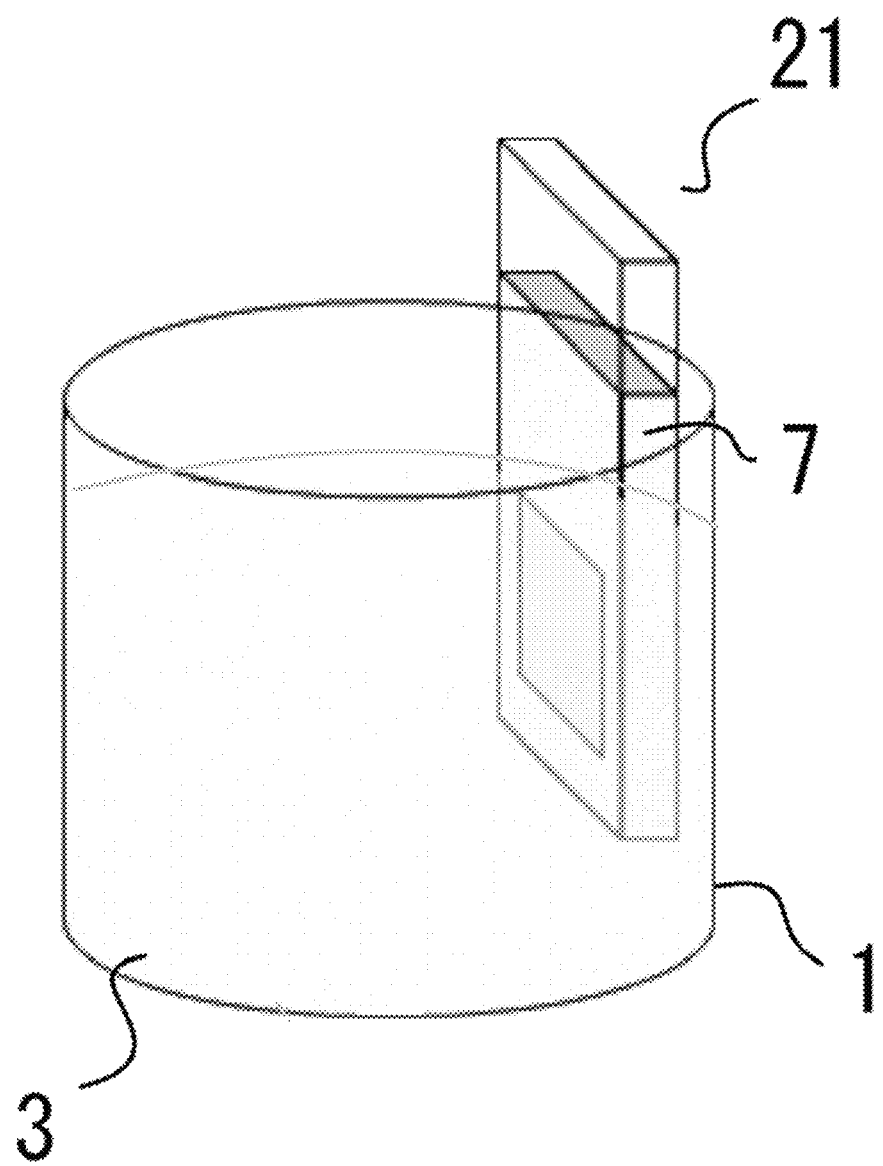

The shape of the measurement cell can be selected so that the measurement cell can be attached to a device to be used. FIG. 7A illustrates an example of a preferred mode of the measurement cell, and FIG. 7B illustrates an example of a mode of a sample solution preparation method using the measurement cell. For convenience of explanation, the shape of the main body 27 of the measurement cell 21 is defined as a rectangle in which two front and back surfaces with a width of 32 mm and a height of 50 mm are connected by two side surfaces and a bottom surface with a thickness of 5 mm, and excitation light transmits the front and back surfaces with a thickness of 1 mm.

The material of the main body 27 can be a resin, such as polypropylene, polyethylene, polymethylpentene, ethylenetetracyclododecene copolymer, polyacetal, acrylonitrile-butadiene-styrene resin, hydroxybenzoate polyester, polyetherimide, methacrylic resin, polyethylene terephthalate, polybutadiene terephthalate, polycyclohexylenedimethylene terephthalate, polyethylene naphthalate, polyacrylonitrile, polystyrene, polyamide, polycarbonate, polyvinyl alcohol, or polylactic acid, glass, quartz or the like, without particular limitation.

Whereas, the measurement cell 21 is formed with a measurement area 23 made of a member that transmits a wavelength within a range of 300 to 800 nm, preferably 400 to 700 nm. If the wavelength transmission is in this range, the degree of fluorescence polarization can be measured without errors. Examples of such a member include glass, quartz, PMMA, PC, COP, COC, and PS.

Further, the measurement cell 21 is provided with a dialysis membrane 25 with a molecular weight cut-off of $2 \times 10^2$ to $2 \times 10^5$, preferably $1.5 \times 10^4$ to $1.4 \times 10^5$. By using the dialysis membrane 25 with the molecular weight cut-off in the above-described range, salts, light scattering materials and other impurities can be effectively removed. A commercially available product can also be used as such a dialysis membrane 25. For example, a dialysis disc or a membrane can be used.

In the measurement cell 21, the position of the measurement area 23 can be formed corresponding to the incoming position of the excitation light of the measurement device used. Since excitation light passes through the measurement cell 21, the measurement area 23 is formed at a part of the front surface and a part of the back surface opposing the corresponding part of the front surface. Further, the dialysis membrane 25 may be arranged in the side surfaces or bottom surface without limitation to the front and back surfaces as long as the dialysis membrane 25 does not overlap the measurement area 23. For example, a measurement cell main body 27 in which the positions for arranging a measurement area 23 and a dialysis membrane 25 are formed as cavities may be prepared in advance, and the measurement area 23 and the dialysis membrane 25 may be installed on the measurement cell 21 by adhesive, welding, fitting or other methods.

As illustrated in FIG. 7B, a dialysis fluid 7 is charged in a measurement cell 21, which is then immersed in a target compound-containing solution 3. After a certain time period, the measurement cell 21 is taken out from the target compound-containing solution 3, and the target compound-containing solution 3 adhering to the outer circumference of the measurement cell 21 is removed. In addition, the outer circumference of the dialysis membrane 25 may be covered with a waterproof film as necessary. To measure the degree of fluorescence polarization P, a fluorescently labeled compound in which the same molecule as the target compound is labeled with a fluorescent substance and an antibody that specifically binds to the target compound are prepared in advance, and these fluorescently labeled compound and antibody are added to the measurement cell 21, before the measurement cell 21 is attached to the measurement device. The degree of fluorescence polarization P can be calculated by exposing the measurement area 23 to excitation light.

A third embodiment of the present disclosure is a measurement kit for measuring the concentration of a target compound selected from a group consisting of a mold poison, a shellfish poison, a chemical used for breeding animals, and a chemical used for growing crops by an immunity analysis method using fluorescence contained in food by an immunity analysis method using fluorescence, the measurement kit comprising:

the measurement cell;
a dialysis fluid to be charged in the measurement cell;
an antibody that specifically binds to the target compound; and
a fluorescently labeled target compound derivative.

Sample preparation and measurement operation can be easily performed when a dialysis fluid is set in a measurement cell that can be used for both preparation of a sample and measurement of the degree of fluorescence polarization. In addition, among immunity analysis methods using fluorescence, FPIA indispensably uses an antibody that specifically binds to a target compound and a fluorescently labeled target compound derivative, based on the principle of competitive binding immunoassay. As such, a measurement kit that further includes an antibody corresponding to a target compound and a target compound derivative in which the target compound is fluorescently labeled is extremely useful.

When such an antibody is commercially available, a commercially available product can be used. On the other hand, even when such an antibody is not commercially available, the antibody can be produced by using an immunogen in which an immunogenic carrier substance is bound to a target compound via an acid amide bond or other group. The immunogenic carrier substance can be selected from conventionally known substances. The immunogenic carrier substance may be any of an immunogenic protein, a polypeptide, a carbohydrate, a polysaccharide, a lipopolysaccharide, a nucleic acid and the like. The immunogenic carrier substance is preferably a protein or a polypeptide, more preferably a bovine serum albumin (BSA), a keyhole limpet hemocyanin (KLH), or a thyroglobulin. Such an immunogen can be used in preparation of polyclonal and monoclonal antibodies by a well-known method. In general, an immunogen, preferably a mixture of an immunogen and an adjuvant, is injected to one or more different sites of a host animal, such as a rabbit, a goat, a mouse, a guinea pig, or a horse. Further injections are conducted at the same or different sites at regular or irregular intervals. The titer is evaluated as necessary to obtain the desired antibody. The antibody can be recovered by collecting blood or the like from the host animal. It should be noted that the antibody in the present disclosure may be a fragment of an immunoglobulin, such as Fab, F(ab')$_2$ or Fv, instead of a complete immunoglobulin. It suffices if at least one epitope of an antibody can bind to a target compound. In addition, a commercially available product may be used for the antibody or fragment.

The target compound derivative can be prepared by binding a fluorescently labeled compound to any of the functional groups of a target compound. Examples of the fluorescently labeled compound include chlorotriazinyl aminofluorescein, 4'-aminomethylfluorescein, 5-aminomethylfluorescein, 6-aminomethylfluorescein, 6-carboxyfluorescein, 5-carboxyfluorescein, 5- and 6-aminofluorescein, thiourea fluorescein, and methoxytriazinyl aminofluorescein. A fluorescently labeled compound can be bound to a target compound using a known method to prepare a target compound derivative.

In the present disclosure, the measurement kit includes a measurement cell in which a dialysis membrane preferable for a target compound is arranged, a target compound derivative corresponding to the target compound, and an antibody that specifically binds to the target compound. The dialysis fluid may come as a set of a plurality kinds of fluids so that an appropriate fluid can be selected depending on a food containing a target compound. Further, the target compound derivative or antibody may be prepared as a liquid reagent by dissolving the target compound derivative or antibody in an appropriate solvent in advance. Furthermore, the measurement kit may include other reagents, standards, buffers, diluents and the like necessary for performing measurement.

A fourth embodiment of the present disclosure is a sample solution preparation device in an immunity analysis method using fluorescence, and the sample solution preparation device comprises:
  a container that receives a target compound-containing solution; and
  one or more dialysis cartridges that are placed in the container,
  wherein the ratio of the total capacity of the dialysis cartridges to the capacity of the container (the total capacity of the dialysis cartridges/the capacity of the container) is within a range of $1/1\times10^4$ to $1/10$. For example, the device is a device in which a dialysis cartridge 5 is arranged in a container 1 as illustrated in FIG. 1. With such a simple structure, the device is preferable for preparing a sample on-site.

Figure 8:
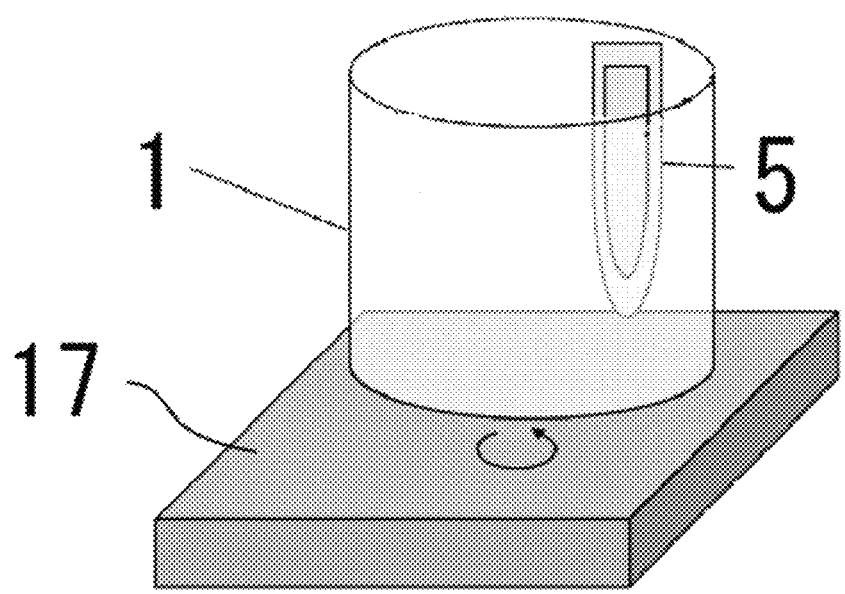
FIG. 8 is a diagram describing an example of a mode in which a sample solution preparation device includes a container, a dialysis cartridge and stirring means.

The container is used for preparing a target compound-containing solution or for receiving a target compound-containing solution for dialysis. The capacity of the container means the total capacity that the container can receive when the container is placed under a normal use condition. Further, the capacity of the dialysis cartridge means the total capacity that the dialysis cartridge can receive when the dialysis cartridge is arranged under a normal use condition. A plurality of dialysis cartridges can also be arranged in the container. When a plurality of dialysis cartridges is arranged, the capacity means the total capacity of the dialysis cartridges. The sample solution preparation device of the present disclosure may be provided with stirring means below the container. FIG. 8 illustrates an example of the sample solution preparation device in which a dialysis cartridge 5 is received in a container 1 and a stirrer 17 is arranged as stirring means below the container 1. The ratio of the total capacity of the dialysis cartridge 5 to the capacity of the container 1 (the total capacity of the dialysis cartridge/the capacity of the container) is within a range of $1/1\times10^4$ to $1/10$, preferably $1/1\times10^4$ to $1/1\times10^2$, more preferably $1/1\times10^3$ to $1/1\times10^2$. Even if it is assumed that a fluid is charged up to 80% of the capacity of the container 1 or the dialysis cartridge 5 in consideration of operability, when the total capacity of the dialysis cartridge 5/the capacity of the container is within a range of $1/1\times10^4$ to $1/10$, the recovered dialysis fluid after dialysis by the dialysis cartridge 5 can have a specific component of substantially the same concentration as the concentration of the specific component contained in the solution charged in the container 1.

Although FIG. 8 illustrates a mode in which a single dialysis cartridge 5 is arranged in a container 1, a plurality of dialysis cartridges 5 may instead be arranged. Further, each dialysis cartridge may have a stopper for anchoring the dialysis cartridge to the container 1 and a lid for preventing leakage of the dialysis fluid through the inlet. The lid may be, for example, a screw type or fitting type. FIG. 9A illustrates a mode in which three dialysis cartridges 5 are arranged, and a dialysis cartridge 5 that has a stopper 5a and a dialysis cartridge 5 that has a lid 5b are received in a container 1. For example, the dialysis cartridge 5 with the lid 5b is charged with a dialysis fluid and covered with the lid 5b, which is then placed together with a target compound-containing solution in the container with a lid. By vibrating the container with the lid from side to side, up and down or the like, distribution between the target compound-containing solution and the dialysis fluid can be ensured without using a stirring device.

Figure 9B:
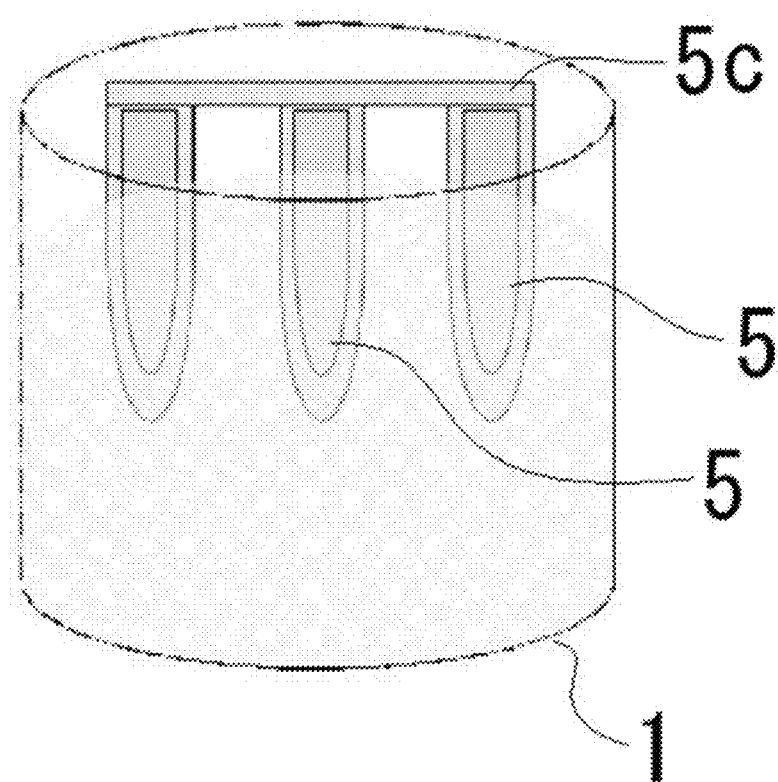
FIG. 9B is a diagram describing a mode in which a sample solution preparation device includes a plurality of dialysis cartridges arranged in a container and the dialysis cartridges are connected to one another by a connecting member.

Further, the plurality of dialysis cartridges may be connected to one another by a connecting member. FIG. 9B illustrates a mode in which three dialysis cartridges 5 are connected by a connecting member 5c and received in a container 1.

Figure 10:
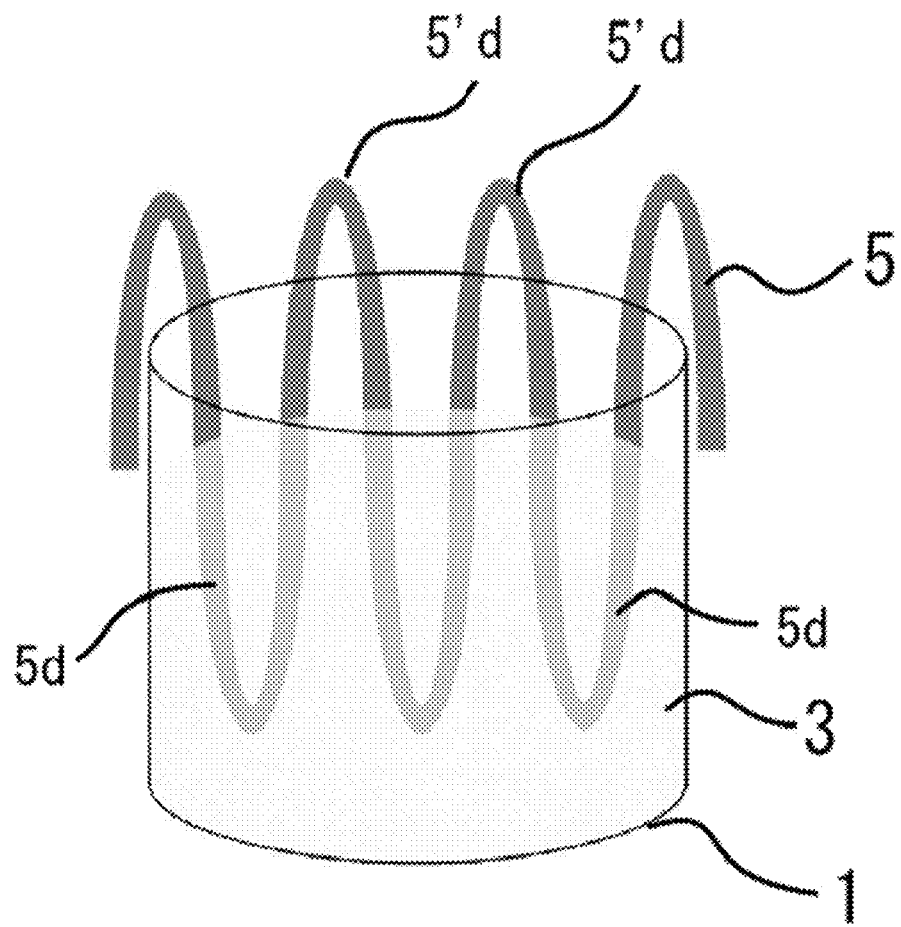
FIG. 10 is a diagram describing a mode in which a sample solution preparation device includes a dialysis cartridge of a long tube shape arranged in a container and the dialysis cartridge comprises a member with dialysis capability and a member without dialysis capability.
Figure 1:
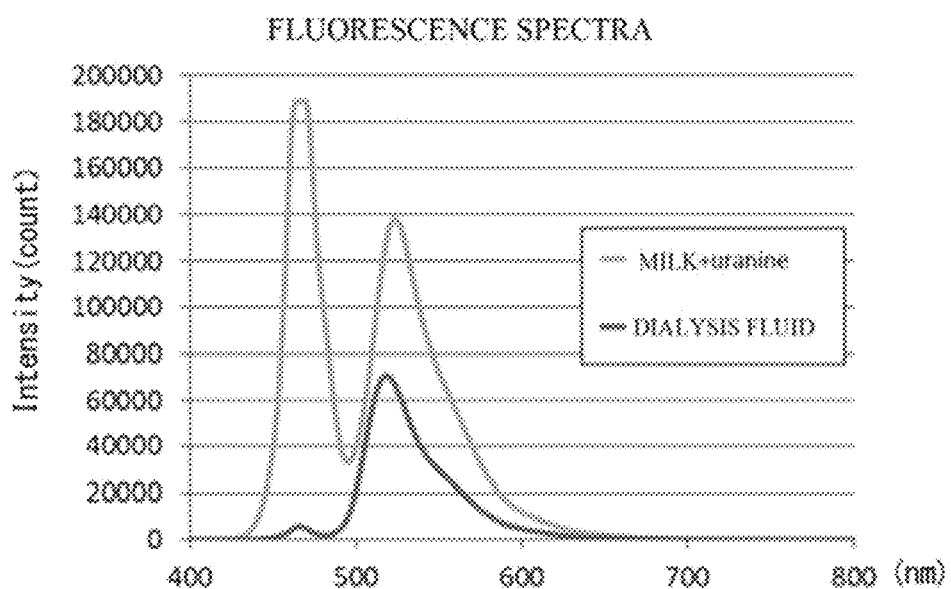
Figure 1:
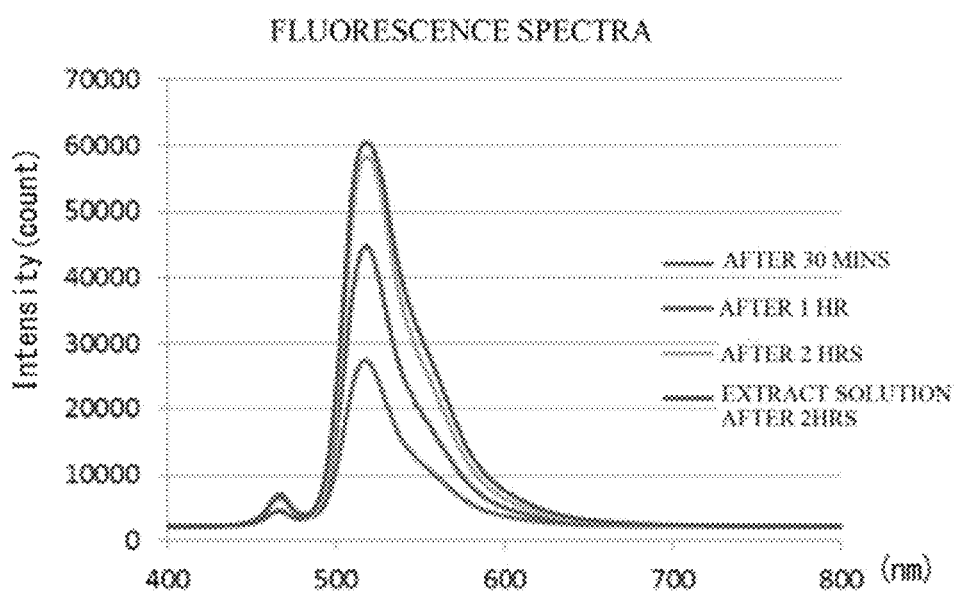

Moreover, the dialysis cartridge may be a long tube shape, over the length of which a dialysis membrane may be arranged or a plurality of membranes may be intermittently connected. FIG. 10 illustrates a mode in which a long tube dialysis cartridge 5 comprises a member 5d with dialysis capability and a member 5'd without dialysis capability, and the member 5d with dialysis capability is arranged in a liquid receiving part of the container 1 and the member 5'd without dialysis capability engages with the upper part of the container 1. As the member with dialysis capability, a dialysis membrane can be used. The molecular weight cut-off is within a range of $2\times10^2$ to $2\times10^5$, preferably $2\times10^3$ to $2\times10^5$, more preferably $2\times10^4$ to $2\times10^5$. The member 5d without dialysis capability may be, for example, polyethylene terephthalate, polyester resin, vinyl resin or the like.

EXAMPLES

The present disclosure will be specifically described below with illustrative Examples, while these examples are not intended to limit the present disclosure in any manner.

Example 1

Seventy milliliters of milk adjusted to a uranine concentration of $1.06\times10^{-4}$ M by adding uranine was prepared and used as a target compound-containing solution. A microdialysis cartridge of 500 μL capacity comprising a dialysis membrane of a molecular weight cut-off of $4\times10^2$ to $1.4\times10^5$ was charged with 300 μL of pure water and immersed in the target compound-containing solution for two hours. After immersion, the fluorescence spectra of the dialysis fluid and target compound-containing solution were observed. The results are illustrated in FIG. 11. It indicates that the target compound-containing solution has peaks at 470 nm and 520 nm, while the dialysis fluid has a main peak at 520 nm, thus, the peak of uranin can be separated by the dialysis membrane.

Example 2

Extract solution was prepared by adding uranin and 70 mL of pure water to 7 g of brown wheat that has been ground by an electric mill to adjust the uranin concentration to $1.06 \times 10^{-4}$ M, which was used as a target compound-containing solution. A micro-dialysis cartridge with a capacity of 300 µL comprising a dialysis membrane with a molecular weight cut-off of $4 \times 10^2$ to $1.4 \times 10^5$ was charged with 300 µL of pure water and immersed in the target compound-containing solution for 2 hours. The fluorescence spectra of the dialysis fluid after 30 minutes, 1 hour, and 2 hours of immersion and the target compound-containing solution after 2 hours of immersion were observed. The results are illustrated in FIG. 12. The peak height the fluorescence spectra of the dialysis fluid increased with immersion time, indicating that the target compound transferred to the dialysis fluid side.

Example 3

Ten grams each of salmon, pork, and carrot were ground in a small mill and respectively received in a filtration membrane with a mesh size of 100 mesh and a capacity of 50 mL. Three containers of 130 mL capacity each received 100 mL of pure water and one of the filtration membranes containing the ground foods.

Figure 13:
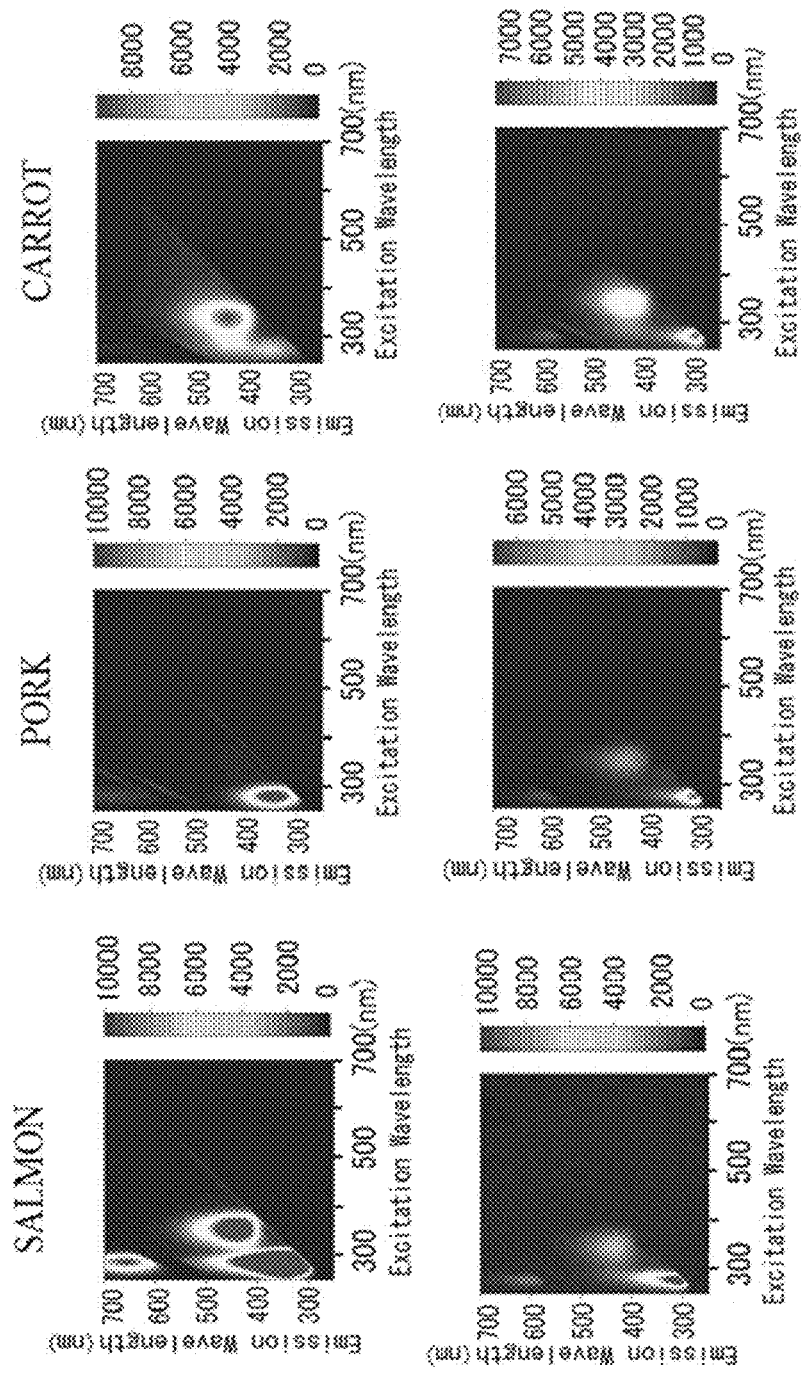
FIG. 13 is a diagram illustrating the results of Example 3.

A micro-dialysis cartridge with a capacity of 300 µL comprising a dialysis membrane with a molecular weight cut-off of $4 \times 10^2$ to $1.4 \times 10^5$ was charged with 300 µL of pure water and immersed in each container for 90 minutes. After immersion, the food extract solutions and dialysis fluids in the containers were recovered and the fluorescence was measured. The results are illustrated in FIG. 13. In the case of any of these foods, the content of fluorescent substance, such as riboflavin, contained in the extract solution was reduced.

Example 4

A sample solution of 110 mL containing chloramphenicol (CAP: molecular weight 323.1) dissolved in pure water at a concentration of 107 ng/mL was received in a container of 130 mL capacity. Four micro dialysis cartridges, each with a capacity of 300 µL and consisting of a dialysis membrane with a molecular weight cut-off of $4 \times 10^2$ to $1.4 \times 10^5$, were respectively charged with 250 µL of pure water as dialysis fluid. After a stirrer chip was put into the container, the sample solution was dialyzed while being agitated with the stirrer. The CAP concentrations in the micro-dialysis cartridges were measured by LC/MS at the beginning of dialysis and after 90, 180, 300, and 1,350 minutes of dialysis. The results are illustrated in Table 1.

TABLE 1

| Elapsed time of dialysis (min) | CAP (ng/mL) |
|---|---|
| 0 | 0 |
| 90 | 42 |
| 180 | 78 |
| 300 | 90 |
| 1,350 | 101 |

Example 5

A sample solution of 110 mL containing chloramphenicol (CAP: molecular weight 323.1) dissolved in milk at a concentration of 112 ng/mL was received in a container of 130 mL capacity. Four micro-dialysis cartridges, each with a capacity of 300 µL and consisting of a dialysis membrane with a molecular weight cut-off of $4 \times 10^2$ to $1.4 \times 10^5$, were respectively charged with 250 µL of pure water as dialysis fluid. After a stirrer chip was put into the container, the sample solution was dialyzed while being agitated with the stirrer. The CAP concentrations in the micro-dialysis cartridges were measured by LC/MS at the beginning of dialysis and after 90, 180, 300, and 1,260 minutes of dialysis. The results are illustrated in Table 2.

TABLE 2

| Elapsed time of dialysis (min) | CAP (ng/mL) |
|---|---|
| 0 | 0 |
| 90 | 45 |
| 180 | 61 |
| 300 | 75 |
| 1,260 | 85 |

According to Example 5, the substance collection rate of the dialysis fluid is lower compared with the substance collection rate from the sample solution using pure water as illustrated in Example 4. However, it was possible to recover chloramphenicol by dialysis even when milk that contains fat and protein was used as a sample solution.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A sample solution preparation method for preparing a sample solution for measuring a concentration of a target compound contained in food by comparing a degree of fluorescence intensity or fluorescence polarization emitted from a fluorescent material with a previously prepared calibration curve in an immunity analysis method using fluorescence, the sample solution preparation method including:
   a dialysis step for bringing a target compound-containing solution that includes the target compound into contact with a dialysis fluid that does not include the fluorescent material through a dialysis membrane to transfer the target compound to the dialysis fluid, and
   an addition step for adding, into the target compound-containing solution after the dialysis step, a fluorescently labeled compound in which the same molecule as the target compound is labeled with a fluorescent substance and an antibody that specifically binds to the target compound, wherein
   a molecular weight cut-off of the dialysis membrane is within a range of $2 \times 10^2$ Da to $2 \times 10^5$ Da, and
   a volume of the dialysis fluid is relatively smaller than a volume of the target compound-containing solution, and a ratio of the volume of the dialysis fluid to the volume of the target compound-containing solution (the volume of the dialysis fluid/the volume of the target compound-containing solution) is within a range of 1/10,000 to 1/10.

2. The sample solution preparation method according to claim 1, wherein the dialysis step is to charge the dialysis fluid in a dialysis cartridge having the dialysis membrane on an outer circumference of the dialysis cartridge and then to immerse the dialysis cartridge in the target compound-containing solution to transfer the target compound to the dialysis fluid.

3. The sample solution preparation method according to claim 1, wherein solubility of the target compound in the dialysis fluid is higher than solubility of the target compound in the target compound-containing solution.

4. The sample solution preparation method according to claim 1, wherein the dialysis step is performed under a condition where, due to heating of the dialysis fluid, a temperature of the dialysis fluid is higher than a temperature of the target compound-containing solution and solubility of the dialysis fluid is increased.

5. The sample solution preparation method according to claim 1, wherein the dialysis step includes:
   comparing a specific gravity of the target compound-containing solution and a specific gravity of the dialysis fluid; and
   pouring, onto the dialysis membrane placed on a surface of one with a higher specific gravity of the target compound-containing solution and the dialysis fluid reserved in a container, the other of the target compound-containing solution and the dialysis fluid, to transfer the target compound to the dialysis fluid.

6. The sample solution preparation method according to claim 1, wherein the dialysis step is performed by adding, in the target compound-containing solution, an impurity adsorbent for adsorbing an impurity having a possibility of causing an error in measurement of fluorescence.

7. The sample solution preparation method according to claim 1, wherein the target compound is one selected from a group consisting of a mold poison, a shellfish poison, a chemical used for breeding animals, and a chemical used for growing crops.

8. The sample solution preparation method according to claim 1, wherein
   the immunity analysis method using fluorescence is fluorescence polarization immunoassay (FPIA), fluorescence-enzyme immunoassay (FEIA), or fluorescent antibody method (FA).

9. The sample solution preparation method according to claim 1, wherein the dialysis fluid consists of pure water.

10. A sample solution preparation method for measuring a concentration of a target compound contained in food by comparing a degree of fluorescence intensity or fluorescence polarization emitted from a label of the target compound with a previously prepared calibration curve in an immunity analysis method using fluorescence, the sample solution preparation method including:
   a dialysis step for bringing a target compound-containing solution that includes the target compound into contact with a dialysis fluid through a dialysis membrane to transfer the target compound to the dialysis fluid, wherein
   a molecular weight cut-off of the dialysis membrane is within a range of $2 \times 10^2$ Da to $2 \times 10^5$ Da,
   a volume of the dialysis fluid is relatively smaller than a volume of the target compound-containing solution, and a ratio of the volume of the dialysis fluid to the volume of the target compound-containing solution (the volume of the dialysis fluid/the volume of the target compound-containing solution) is within a range of 1/10,000 to 1/10, and
   the dialysis step is performed while agitating, with a stirrer chip, at least one of the target compound-containing solution or the dialysis fluid, the stirrer chip including silver-coated iron oxide particles or silver-iron oxide particles.

* * * * *